(12) United States Patent
Sawosz Chwalibog et al.

(10) Patent No.: US 10,471,095 B2
(45) Date of Patent: Nov. 12, 2019

(54) SUSPENSION OF GRAPHENE OXIDE NANOFLAKES IN WATER, ITS USE AND A METHOD OF PREPARATION THEREOF

(71) Applicants: Szkola Glowna Gospodarstwa Wiejskiego, Warsaw (PL); Instytut Technologii Materialow Elektronicznych, Warsaw (PL)

(72) Inventors: Ewa Sawosz Chwalibog, Zgorzala (PL); Marta Kutwin, Radom (PL); Slawomir Jaworski, Przylek (PL); Mateusz Wierzbicki, Warsaw (PL); Marta Grodzik, Kobylka (PL); Anna Hotowy, Brwinow (PL); Ludwika Lipinska, Warsaw (PL); Joanna Jagiello, Ryki (PL)

(73) Assignees: SZKOLA GLOWNA GOSPODARSTWA WIEJSKIEGO, Warsaw (PL); INSTYTUT TECHNOLOGII MATERIALOW ELEKTRONICZNYCH, Warsaw (PL)

( * ) Notice: Subject to any disclaimer, the term of this patent is extended or adjusted under 35 U.S.C. 154(b) by 118 days.

(21) Appl. No.: 15/119,099

(22) PCT Filed: Feb. 5, 2015

(86) PCT No.: PCT/EP2015/052429
§ 371 (c)(1),
(2) Date: Aug. 15, 2016

(87) PCT Pub. No.: WO2015/121150
PCT Pub. Date: Aug. 20, 2015

(65) Prior Publication Data
US 2017/0049814 A1    Feb. 23, 2017

(30) Foreign Application Priority Data
Feb. 13, 2014 (PL) .................. 407166

(51) Int. Cl.
| | | |
|---|---|---|
| A61K 33/24 | (2019.01) | |
| C07F 15/00 | (2006.01) | |
| A61K 31/336 | (2006.01) | |
| A61K 9/00 | (2006.01) | |
| A61K 9/10 | (2006.01) | |
| C01B 32/20 | (2017.01) | |
| C01B 32/182 | (2017.01) | |

(52) U.S. Cl.
CPC ............ *A61K 33/24* (2013.01); *A61K 9/0019* (2013.01); *A61K 9/10* (2013.01); *A61K 31/336* (2013.01); *C01B 32/182* (2017.08); *C01B 32/20* (2017.08); *C07F 15/0086* (2013.01)

(58) Field of Classification Search
None
See application file for complete search history.

(56) References Cited

FOREIGN PATENT DOCUMENTS

CN       103558170 A    2/2014

OTHER PUBLICATIONS

Zhang, W., et al., Biomaterials 32: 8555-8561 (2011).*
Wahab, R., et al., Journal of Biomedical Nanotechnology 8: 424-431 (2012).*
WIPO, International Search Report for International Application PCT/EP2015/052429, dated May 11, 2015, 4 pages.
WIPO, Written Opinion for International Application PCT/EP2015/052429, dated May 11, 2015, 6 pages.
Chang Han-Wei et al., "Preparation of graphene-supported platinum nanoparticles in aqueous solution by femtosecond laser pulses for methanol oxidation", Journal of Power Sources, Elsevier SA, CH, vol. 239, pp. 164-168, Apr. 1, 2013.
Database WPI, Thomson Scientific, London, GB.
Yutaka Miura et al., "Cyclic RGD-Linked Polymeric Micelles for Targeted Delivery of Platinum Anticancer Drugs to Glioblastoma through the Blood-Brain Tumor Barrier", ACS NANO, vol. 7, No. 10, pp. 8583-8592, Oct. 22, 2013.
Andre Chwalibog et al., "In vitro and in vivo effects of graphene oxide and reduced graphene oxide on glioblastoma", International Journal of Nanomedicine, p. 1585, Feb. 25, 2015.

* cited by examiner

*Primary Examiner* — David J Blanchard
*Assistant Examiner* — Daniel F. Coughlin
(74) *Attorney, Agent, or Firm* — Masuvalley & Partners (57) ABSTRACT

The present invention relates to a water suspension of graphene oxide nanoflakes decorated by nanoparticles of metallic platinum, characterised in that it comprises: • 100 µg/ml to 500 µg/ml of graphene oxide nanoflakes, • 5 µg/ml to 50 µg/ml of nanoparticles of metallic platinum (Pt°), deposited on the surface of graphene oxide nanoflakes. The invention also relates to a method of preparing such suspension and its use as an antitumor agent.

1 Claim, 5 Drawing Sheets

| Group | Weight (g) | % |
|---|---|---|
| Control, k | 0.2303 | 100 |
| Graphene oxide + nanoPt, gnpt | 0.1308 | 56.795 |

SUSPENSION OF GRAPHENE OXIDE NANOFLAKES IN WATER, ITS USE AND A METHOD OF PREPARATION THEREOF

RELATED APPLICATIONS

This application is the U.S. National Phase of and claims priority to International Patent Application No. PCT/EP2015/052429, International Filing Date Feb. 5, 2015, entitled Suspension Of Graphene Oxide Nanoflakes In Water, Its Use And A Method Of Preparation Thereof, which claims benefit of Poland Application No. P.407166 filed Feb. 13, 2014 entitled Suspension Of Graphene Oxide Nanoflakes In Water, Its Use And A Method Of Preparation Thereof, all of which are incorporated herein by reference in their entireties.

The object of the invention is a suspension of graphene oxide (GO) nanoflakes in water. More specifically, the present suspension can be also defined by a composite composed of graphene oxide nanoflakes decorated with nanoparticles of platinum metal) ($Pt^\circ$) which are suspended in water (for simplicity referred to as "GO/$Pt^\circ$ suspension"). The invention also relates to the use of this suspension as a multifunctional antitumor agent, and it also covers a method of preparation of this suspension.

Graphene oxide (GO) is a specific chemical compound having an oxygen content varying within wide limits from several to several tens of percent by weight. Its structure is a flat layer of carbon atoms located in the corners of hexagon, to which a plurality of functional groups are attached, e.g. carboxyl, hydroxyl, epoxy groups, responsible for highly hydrophilic properties of this material. Graphene oxide is obtained as a result of intercalation and oxidation of flake graphite, most often by Hummers method [1] or its modifications [2, 3]. Due to its highly developed surface (the theoretical specific surface area is about 2600 $m^2/g$), graphene oxide has a very high adsorption capacity in relation to different chemical compounds: organic solvents, dyes, aromatic compounds, heavy metal ions [4]. It is also an excellent platform for deposition of metal nanoparticles (e.g. Ag, Au, Pt, Pd) [5] and metal oxides (e.g. $Fe_3O_4$, $TiO_2$ $Co_3O_4$) [6], allowing preparation of composites exhibiting excellent catalytic properties. Among them, graphene oxide/platinum nanoparticles (GO/$Pt^\circ$) composites occupy a special place. They exhibit strong electrocatalytic properties of methanol oxidation and oxygen reduction, which allows them to be used as membranes in hydrogen fuel cells [7-10] or dye solar cells [11-12]. This type of composites is also applicable in electrochemical sensors of, e.g., glucose, hydrogen peroxide [13-14].

So far, graphene oxide/platinum nanoparticle composite was not used in medicine, for therapy of tumours. A method of preparation thereof is also an innovative solution. In the mentioned publications [7-14], GO/$Pt^\circ$ was obtained at the time of simultaneous reduction of graphene oxide and platinum ions introduced to the solution as hexachloroplatinic acid $H_2PtCl_6$. Various chemical compounds reducers, and functionalising compounds which prevent agglomeration of graphene flakes are used for the reduction. It is then very difficult to remove by-products of the reduction due to the above-mentioned great adsorption capacity of graphene.

Meanwhile, in the invention being applied, the present suspension is obtained by combining pure suspension of graphene oxide and colloidal solution of pure metallic platinum, with simultaneous use of ultrasonic energy. This method is superior to the one described in articles [7-14] as it allows obtaining very pure material, which is of crucial importance when it is administered to living organisms. Further, metallic platinum is immobilised (by van der Waals forces) on the surface of graphene oxide flakes, which prevents its spreading to the surrounding tissues. However, in tumour therapy known in the prior art, with the use of platinum complexes, such spreading occurs, which is detrimental to the patient.

Complex compounds of platinum, as an achievement of coordination chemistry, have been used in tumour chemotherapy. Popularisation of the use of complex compounds of platinum took place in the 1970's, and they were qualified to cytostatic medicines exhibiting an alkylating activity. Within the last 50 years, approx. 3000 complex compounds of platinum were synthesized, among which 30 reached the stage of clinical studies, and only 6 compounds, i.e. cisplatin, carboplatin, oxaliplatin, nedaplatin, lobaplatin, heptaplatin, were approved worldwide to be used in the treatment of tumours. Cisplatin and carboplatin are used to treat, among others, tumours of the head [15, 16, 17, 18].

All known medicines are salts of platinum or their derivatives, where platinum is present in the form of cation, and not in the form of metal $Pt^\circ$.

Mechanism of medicines based on platinum salts consists in formation of bonds with the DNA, which ultimately inhibits proliferation of tumour cells. Medicines—platinum complexes introduced into the organism are hydrolysed to active dihydroxy-cis-diamineplatinum(II) or dihydroxy-trans-cyclohexanediamine platinum which react with DNA. Platinum salts act on the principle of nucleophilic substitution, incorporating platinum atoms in the place of guanine N(7) atom or less often adenine N(1), N(3) atoms or cytosine N(3) atom [19]. The basis of the mechanism of platinum salts is to form intra-strand, inter-strand bifunctional cross bonds within the DNA strand. Pt—N(7) bond in guanine, as a very strong one, is to the greatest extent responsible for cytotoxic activity of medicines. The result of this mechanism is formation of DNA adducts, which is a direct cause of inhibition of replication processes of genetic material in tumour cells [20-22]. This damage, recognised by HMG proteins, induces an apoptotic pathway in the cell.

However, the use of platinum complexes in antitumor therapy involves significant disadvantages in the form of side effects observed, mentioned below:

Toxic effects on healthy cells, especially rapidly dividing healthy cells. The main adverse activities resulting from the use of complex compounds of platinum are: hepatotoxicity, neurotoxicity, nephrotoxicity, ototoxicity, bone marrow suppression and others.

The main route of administration of platinum complexes in the form of salts are intravenous infusions in the form of drops, which influences the toxic effect of platinum salts on morphotic elements of blood and wide distribution in the organism.

As salts, they can easily and quickly react with multiple molecules of a living organism, which results in the formation of toxic compounds and involvement of medicines in side reactions, which reduces the effectiveness of medicine.

Induction of resistance to platinum:
reducing susceptibility of medicines to formation of chemical bonds which block the activity of medicine, during its transport in the organism, and in particular the formation of strong complexes with albumins, metallothioneins;
preventing activation of mechanisms of intracellular resistance, such as increasing tolerance to DNA damages, overexpression of anti-apoptotic proteins;

formation of complexes with a net positive charge, which increases the efficiency of formation of reactions with DNA;

formation of compounds with increased lipophilicity, which allows an increase in the activity of passive transport of medicine;

use of encapsulation which protects platinum complexes against premature reactivity;

use of bacteria as mini-cells protecting platinum complexes against premature reactivity;

use of nanotubes as "drug delivery system", which use clathrin-dependent transport mechanism to the cell;

photochemical activation.

The present inventors were the first to obtain an ultra-clean hydro-suspension of graphene oxide nanoflakes decorated with nanoparticles of metallic platinum and unexpectedly found its high effectiveness as a multifunctional antitumor agent.

Therefore, the object of the present invention is to propose a new suspension, method of its preparation and its use as a multifunctional antitumor agent.

The water suspension of graphene oxide nanoflakes decorated by nanoparticles of metallic platinum, according to the invention, is characterised in that it comprises:

100 µg/ml to 500 µg/ml of graphene oxide nanoflakes,

5 µg/ml to 50 µg/ml of nanoparticles of metallic platinum (Pe), deposited on the surface of graphene oxide nanoflakes.

Preferably, the suspension comprises 200 µg/ml to 250 µg/ml of graphene oxide nanoflakes.

Preferably, the graphene oxide nanoflakes have linear dimensions from 10 nm to 200 µm, more preferably from 100 nm to 50 µm, and most preferably from 300 nm to 20 µm, have a thickness from 0.5 nm to 10 nm, more preferably from 0.5 nm to 3 nm, and the oxygen percentage ranges from 5 to 50% by weight, more preferably from 15 to 50% by weight.

Preferably, the suspension comprises 10 µg/ml to 20 µg/ml of nanoparticles of metallic platinum (Pe), and most preferably 10 µg/ml to 15 µg/ml of nanoparticles of metallic platinum (Pe).

Preferably, the nanoparticles of metallic platinum (Pe) have linear dimensions from 1 nm to 100 nm, more preferably from 1 nm to 25 nm, and most preferably about 10 nm.

Preferably, the weight ratio of nanoparticles of platinum (Pe) to nanoflakes of graphene oxide ranges from 2:100 to 50:100, and most preferably is 4:100.

Preferably, the suspension according to the invention comprises: nanoflakes of graphene oxide and nanoparticles of metallic platinum (Pe), both suspended in the water, the said nanoparticles being deposited on the surface of nanoflakes of graphene oxide, characterised above, i.e. it does not contain any other ingredients besides those.

The invention also includes the use of this suspension as an antitumor agent, especially against human or animal tumours.

Preferably, this use involves direct injection of the suspension into the tumour or directly near to the tumor.

The object of the invention is also a method of preparation of the suspension of graphene oxide nanoflakes in water, characterised in that it includes the following steps:

a) combining pure suspension of graphene oxide in water with pure colloidal solution of metallic platinum in water, with optional stirring, b) treating the mixture thus obtained by an ultrasonication process, preferably in an ultrasound bath, preferably for a period of 30 to 60 minutes, more preferably for about 45 minutes.

Summary of the invention is a system comprising nanoparticles of platinum (Pt°), attached to graphene oxide nanoflakes by weak non-covalent bonds, suspended in ultra pure water, intended to be administered directly into the tumour tissue and the surrounding area.

Characteristics of particular components of the suspension is as follows:

Platinum Nanoparticles platinum nanoparticles having a purity of platinum above 99.95% (more preferably 99.99%) may be obtained:

1. in the form of powder having a purity of at least 99.9%
2. colloid of platinum nanoparticles having a purity above 99.95% (better 99.99%) in ultra pure water.

In the first case, the platinum powder is suspended in water in order to obtain an aqueous colloid of platinum nanoparticles. The platinum powder is suspended in water by adding the platinum nanoparticles in the amount of 10 µg to 50 µg of powder of Pt° nanoparticles per 1 ml of water, most preferably 10 µg-30 µg is added, less preferably 31 µg-40 µg is added, and least preferably 41 µg-50 µg is added. The process of forming colloid and of preventing formation of aggregates is supported by stirring and by an ultrasonic treatment. In both cases, the water should be ultra pure (resistance of 18.2 MΩ×cm at 25° C.), at the level of biological/chemical contamination not exceeding 0.0001% in solution and deprived of ions. The size of platinum nanoparticles ranges up to 100 nm. The effectiveness of the composite increases with a decrease in the size of platinum nanoparticles, and the most preferred size of the platinum nanoparticles ranges up to 10 nm. The size of platinum nanoparticles was studied with the use of transmission electron microscopy, scanning electron microscopy and by DLS (Dynamic Light Scattering) method. Concentration of the aqueous colloid of platinum, as a starting solution used to produce a multifunctional complex of graphene oxide flakes and Pt° platinum nanoparticles of 50 µg/ml.

Nanoflakes of Graphene Oxide

Nanoflakes of graphene oxide used for the preparation of ultra pure suspension have linear dimensions of 10 nm to 100 µm, and even 200 µm, and their thickness is of the order of several nanometres (generally in the range of 0.5 nm to 10 nm). The oxygen content is from several to fifty percent by weight.

Water

Dispersion phase is constituted by ultra pure water at the level of biological/chemical contamination not exceeding 0.0001% in solution and deprived of ions. The ultra pure water is the only possible medium in which it is possible to produce a multifunctional system of nano Pt/graphene oxide nanoflakes.

PREFERRED EMBODIMENTS OF THE INVENTION

Now, the invention will be presented in greater detail in preferred embodiments, with reference to the accompanying drawings which show.

PREPARATION OF THE SUSPENSION ACCORDING TO THE INVENTION

Flakes of graphene oxide in the amount of 100 μg to 500 μg are suspended in an aqueous colloid of platinum nanoparticles with a platinum concentration of 50 μg/ml to 10 μg/ml of water by stirring and an ultrasonic treatment for 45 mins (in apparatus Ultron U 509 (Zakład Urządzeń Elektronicznych) at the temperature of 20-25° C.).

Platinum nanoparticles were obtained most often by purchasing them at Nano-Tech sp. z o. o., Warsaw, Grzybowska 16/22 or at Nanokoloid, or at Sigma Aldrich. The most preferred effect was observed for platinum nanoparticles purchased at Nanokoloid.

The final weight ratio of platinum nanoparticles to graphene oxide nanoflakes ranged from 50:100 to 2:100. The most preferred effect is observed for the ratio of 4:100.

Process of preparing GO/Pt° suspension is controlled by visualisation in electron microscope TEM JEM-1220 (JEOL, Tokyo, Japan) 80 KeV, compatible with Morada eleven-megapixel camera (Olympus Soft Imaging Solutions, Munster, Germany) using 10 repetitions×100 images. Further, Zeta potential measurement was used, with 5 repetitions×10-100 analyzes (Nano-Z590, Malvern, Worcestershire, UK).

Example 1

Preparation of Suspensions According to the Invention

By the above-described method, suspensions of graphene oxide flakes decorated with platinum nanoparticles in various proportions were prepared, including:

Experiment 1

Platinum Nanoparticles in Powder Form

In sterile tubes (250 ml), 100 ml of water taken from Millipore water station was measured, and then 50 μg of platinum nanoparticle powder, purchased at Sigma Aldrich, was measured and added to the water. The sample was stirred for 1 hour at room temperature, and then subjected to ultrasonic treatment in an ultrasound bath for example, but not limited to: in apparatus Ultron U 509 (Zakład Urządzeń Elektronicznych, PL). Prepared colloid of platinum nanoparticles was studied with the use of scanning electron microscopy and an apparatus for measuring Zeta potential and nanoparticle size (Nano—ZS90, Malvern, Worcestershire, UK), similarly to the proceedings for the purchased aqueous Pt nanoparticle colloids.

Measurement results of the size distribution of nanoparticles in the colloids obtained were similar for all the studied colloids and were on average; nanoparticles with dimensions of up to 10 nm constituted 11%; nanoparticles with dimensions of 10-30 nm constituted 21%; nanoparticles with dimensions of 30-60 nm constituted 57%; nanoparticles with dimensions of 60-100 nm constituted 11%.

As a result of the experiment, stable colloids of platinum nanoparticles in water with a concentration of 50 μg/ml were obtained, which were then used to produce suspensions of graphene oxide nanoflakes decorated with platinum nanoparticles.

Experiment 2

The following were used:
Aqueous colloids of platinum nanoparticles obtained from Nano-Tech (NT), Aqueous colloids of platinum nanoparticles obtained from Nanokoloid (NK), Aqueous colloids of platinum nanoparticles prepared in own laboratory from platinum nanoparticles purchased at Sigma Aldrich (experiment/example 1) (SA),
Powder of graphene oxide flakes produced in ITME.
All the colloids of platinum nanoparticles were used at concentration levels of 50 μg/ml and 10 μg/ml.

In sterile tubes (250 ml), 100 ml for each of the particular colloids (NT, NK, SA) was measured on two concentration levels of platinum nanoparticles (50 μg/ml and 10 μg/ml), and powder of graphene oxide flakes in the amount of 100 μg/ml and 500 μg/ml was added to each of 6 samples, thus obtaining 12 different groups. The samples were stirred for 1 hour at room temperature, and then subjected to ultrasonic treatment in apparatus Ultron U 509 (Zakład Urządzeń Elektronicznych PL).

The obtained colloids of graphene nanoflakes decorated with platinum nanoparticles were studied with the use of scanning electron microscopy and an apparatus for measuring Zeta potential and nanoparticle size (Nano-ZS90, Malvern, Worcestershire, UK).

The results of the study showed that stable colloids were obtained in all of the studied groups. Zeta potential of the samples ranged from −12.3 to −19.7; size distribution of nanoparticle colloids exhibited the presence of large molecules characteristic for graphene. Microscopic observation revealed that graphene oxide nanoflakes are decorated with platinum nanoparticles on their surface in an unordered manner. Platinum nanoparticles were only on the surface of graphene oxide flakes which indicated high affinity of these two structures and that all platinum nanoparticles were attached to graphene oxide. On the surface of graphene oxide flakes, the number of platinum nanoparticles directly proportional depending on the concentration of colloids of platinum nanoparticles and inversely proportional depending on the amount of added powder of graphene oxide flakes was observed. The results of the study are presented in FIG. 1.

Platinum nanoparticles are bound by a weak non-covalent binding with graphene oxide flakes. The process of creating these bonds is the result of forced self-organisation under the influence of ultrasounds in an ultrasound bath for example, but not limited to: in apparatus Ultron U 509 (Zakład Urządzeń Elektronicznych PL) for 45 mins and at the temperature of 25° C.

Example 2

Study on Antitumour Properties of GO/Pt° Suspension

Biological models: study was conducted on models: 1. Chicken embryo maintained by in ovo method, which above all allowed for fast, accurate and insightful observations of potential toxicity, especially embryotoxicity of graphene oxide and Pt nanoparticles of various concentrations. 2. Glioblastoma multiforme GM (U-87) cell lines in order to observe basic mechanisms occurring in the cells under the influence of graphene oxide and platinum nanoparticles and having selected the used experimental factors 3. Glioblastoma multiforme (U-87) tumour grown by in ovo method in order to confirm or reject the preliminary results. This study allowed for the final verification of formulated hypotheses.

Design of Experiments

Step I—preliminary study—determination of potential toxic properties of graphene oxide and nano-Pt in contact with a living organism (chicken embryo)

Determination of the influence of graphene oxide and nano-Pt on homeostasis of the organism of chicken embryo (survival rate, growth and development, biochemical and morphological indicators of blood, expression of selected genes, image of microstructure and ultrastructure of the brain, apoptosis/necrosis and others). 8 experiments were conducted, in which it was found that:
1. graphene oxide administered in the amount of up to 100 μg/ml decreases survival rate of embryos by about 10%, does not exhibit toxic effects on the level of analysis of biochemical and morphological indicators of blood, FGF, VEGF, PCNA gene expression, image of microstructure and ultrastructure of the brain and liver;
2. graphene oxide, administered to the rats by intraperitoneal injection for 4 weeks, 8×dose of 4 mg of graphene/kgBW/day, does not influence growth, health and behavior of animals. Graphene was deposited directly at the place of administration, without tendency to migration, even after 4 month. The packages of graphene do not induce inflammation, irritation and any other side effects.
3. platinum nanoparticles administered in the amount of up to 20 μg/ml did not negatively affect survival rate, growth and development of chicken embryos. In neurotoxicity study, any negative impact of Pt nanoparticles on the number of cells of cerebral cortex was not found although a slight degradation of mitochondria was observed. Platinum nanoparticles affected the activation of apoptosis and a slight decrease in the rate of brain cell proliferation. The study indicated a potential antitumor effect of Pt nanoparticles and a low degree of toxicity [23].

Figure 1:
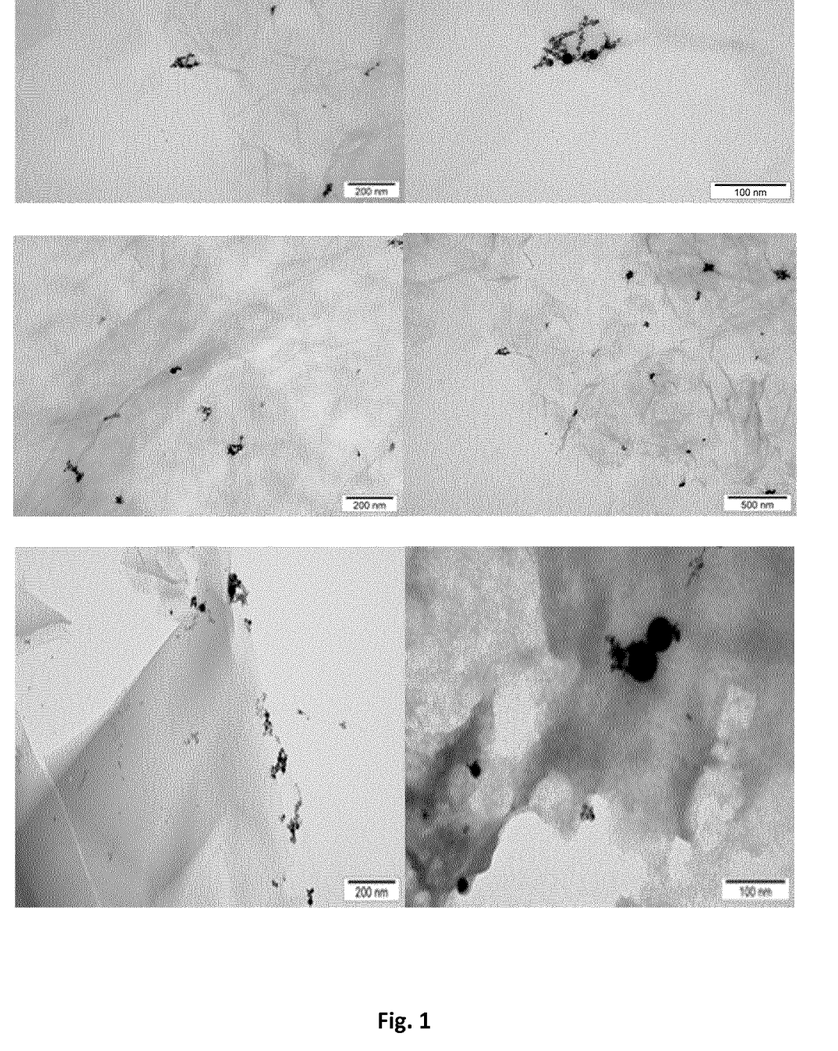
FIG. 1—visualisation of the suspension of graphene oxide flakes decorated with platinum nanoparticles, obtained from Nanokoloid (NK), Nanotech (NT) and Sigma Aldrich (SA) in different ratio of graphene oxide to platinum nanoparticles (G:Pt, µl) A (NK)—2:100; B (NK)—2:100; C (NK)—2:100; D (NK)—50:100; E (NT)—50:100, F(SA)—50:100.
Figure 2:
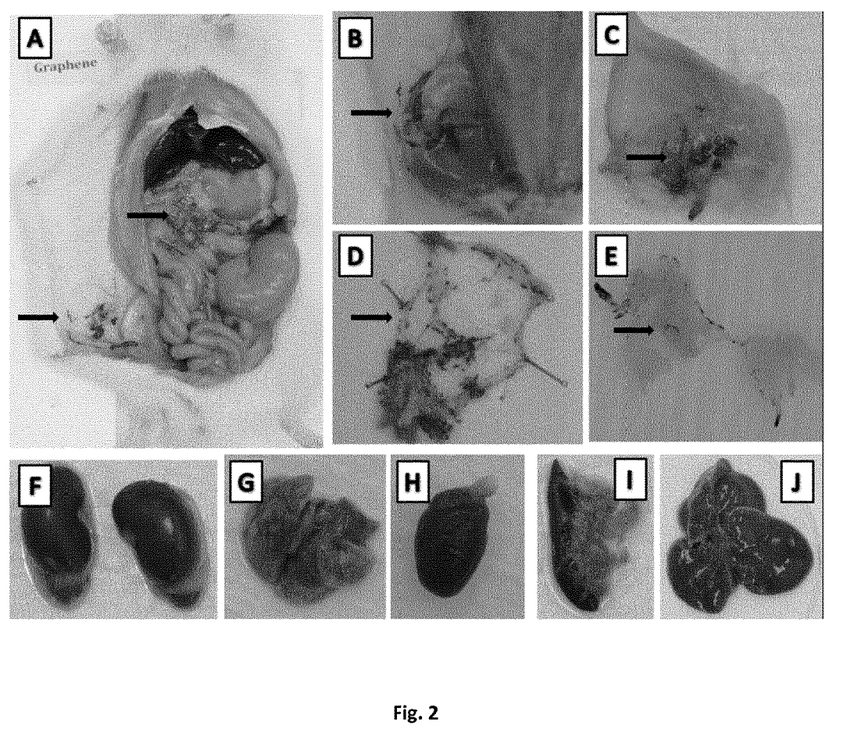
FIG. 2—Visualization of the bio-distribution of graphene oxide nanoparticles after multiple intraperitoneal injection to rats, after 4 month. Solid packages are placed in the injection body regions (A, B, C) and mesentery (D). The macroscopic structure of main organs like kidney (F), lungs (G), heart (H), spleen (I) and liver (J) is proper, without pathological features. Black arrows indicate the aggregates of graphene oxide nanoparticles.

Step II—comparative study—determination of the effect of the suspension of graphene oxide and Pt as compared to cisplatin Determination of toxicity of graphene oxide flakes and platinum nanoparticles with respect to the cells of glioblastoma multiforme of U-87 and U-118 lines. 10 experiments were conducted, in which it was found that:
1. Graphene oxide nanoflakes exhibited very high affinity and ability of adhesion to cell membrane of cell bodies. Death rate of GM cells upon contact with graphene oxide flakes was proportional to its concentration, and with a concentration of 100 μ/ml, it was 42% for GM U-87 cells, and 52% for GM U-118 cells. A significant disintegration of cell membrane was also found. As a result, it was found that graphene nanoflakes were the cause of apoptosis of glioblastoma cells in 67.5% in GM U-87 cells and in 99% in GM U-118 cells. Moreover, genotoxic effect was also observed, as a consequence of penetration of cells by graphene platelets [24]. To sum up, graphene oxide nanoflakes exhibit antitumor activity, as determined based on in vivo study on U-87, U-118 cells of glioblastoma multiforme. Tests on death rate, viability, membrane integrity, proliferation rate, DNA degradation exhibited toxic effects of graphene oxide nanoflakes on glioblastoma multiforme cells [25, 26].
2. Pt° platinum nanoparticles as compared to cisplatin affected, to a similar extent, cell survival rate, integrity of cell membranes, proliferation rate of cells and death rate; applied dose of platinum (as an element) for both administrations were on the same level. As a result of the use of hydrocolloid of platinum nanoparticles in the form of direct injection into the tumour tissue, a significant reduction in tumour weight and volume and activation of apoptosis signalling pathways were observed (FIG. 1).

Step III—summarising study—determination of the effect of the suspension of graphene oxide and platinum nanoparticles (GO/Pt°) on the morphology of glioblastoma multiforme tumour, and determination of mechanisms of antitumor activity on the level of protein, gene expression and visualization of microstructure and ultrastructure of the tumour tissue.

Preparation of Graphene-Pt complexes as "drug delivery system" by the method of forced self-organisation verified by TEM, SEM visualisations and Zeta potential, UV absorbance).

24 experiments in 2 repetitions were conducted, and a high affinity of platinum nanoparticles to graphene oxide nanoflakes was found, independently of the concentration used, chaotic decoration of graphene oxide nanoflakes by platinum metal nanoparticles, sustainability of the suspensions prepared.

Figure 3:
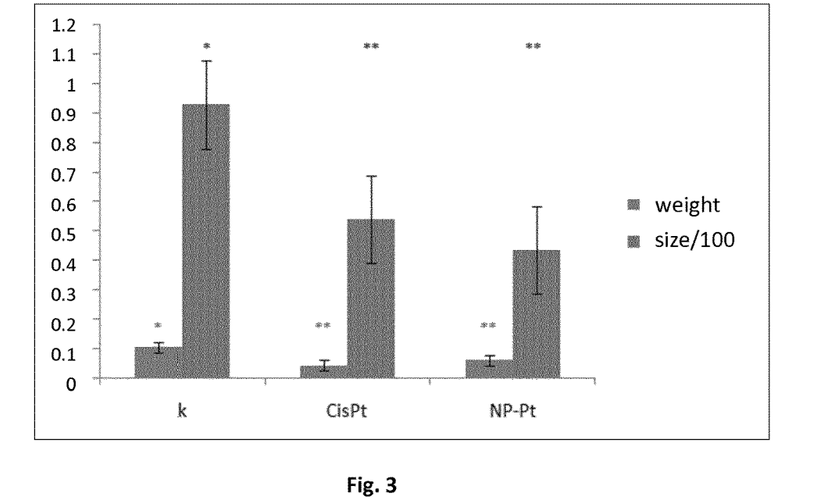
FIG. 3—illustration of the impact of nanoparticles of platinum (3 μg/ml) and cisplatin (4 μg/ml), administered via direct injection into the tumour tissue, on the weight and dimensions of glioblastoma tumours obtained with the use of in ovo techniques. *,** indicate statistically significant differences between the studied groups. p-value <0.005, blue bar (on the left)—weight, pink bar (on the right)—size/100, FIG. 4—preparation of a piece (sample) of GM tumour in a confocal microscopy image. Visualization of caspase 9 (green colour) on the background of cell nuclei (blue colour) in the preparation of GM tumour under the influence of administering the suspension of graphene oxide decorated with Pt nanoparticles, FIG. 5—preparation of a piece (sample) of GM tumour in a confocal microscopy image. Visualization of NFkB (kB nuclear factor) (green colour) on the background of cell nuclei (blue colour) in the preparation of GM tumour under the influence of administering the suspension of graphene oxide decorated with Pt nanoparticles, FIG. 6—graph of tumour weight (average) of glioblastoma multiforme in the control group (k), tumour weight (average) in the group treated by administering the suspension of graphene oxide decorated with Pt nanoparticles, FIG. 7—photographs of selected glioblastoma multiforme tumours of U-87 line from control groups, and FIG. 8—photographs of selected glioblastoma multiforme tumours of U-87 line from groups treated with the suspension of graphene oxide decorated with Pt nanoparticles. Visible reduction of blood vessels and reduced average tumour weight.
Figure 4:
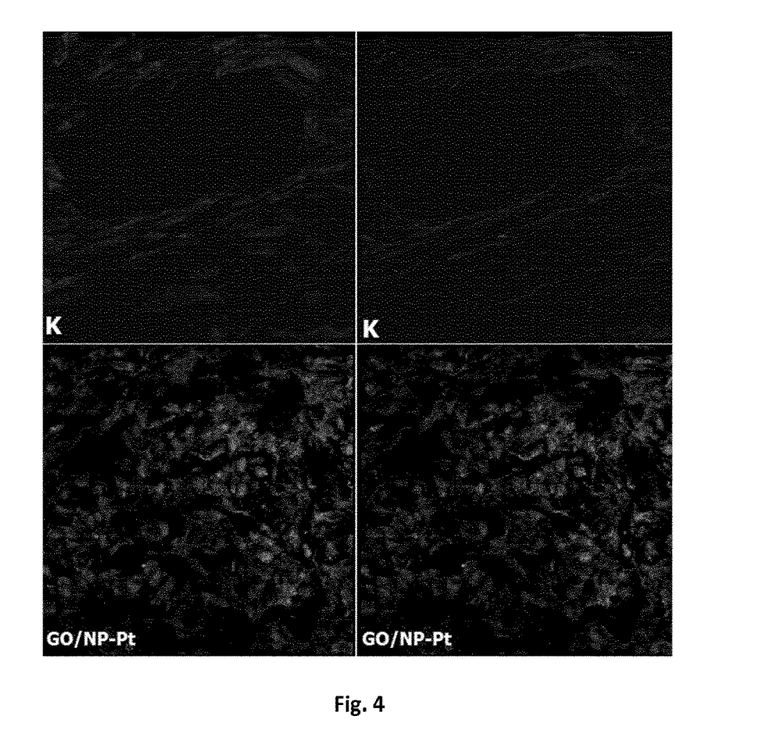
Figure 5:
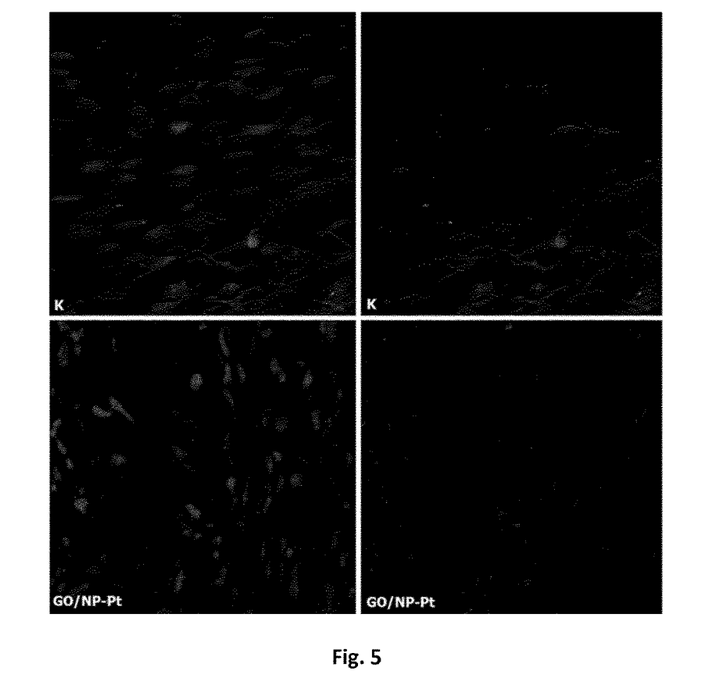
Figure 6:
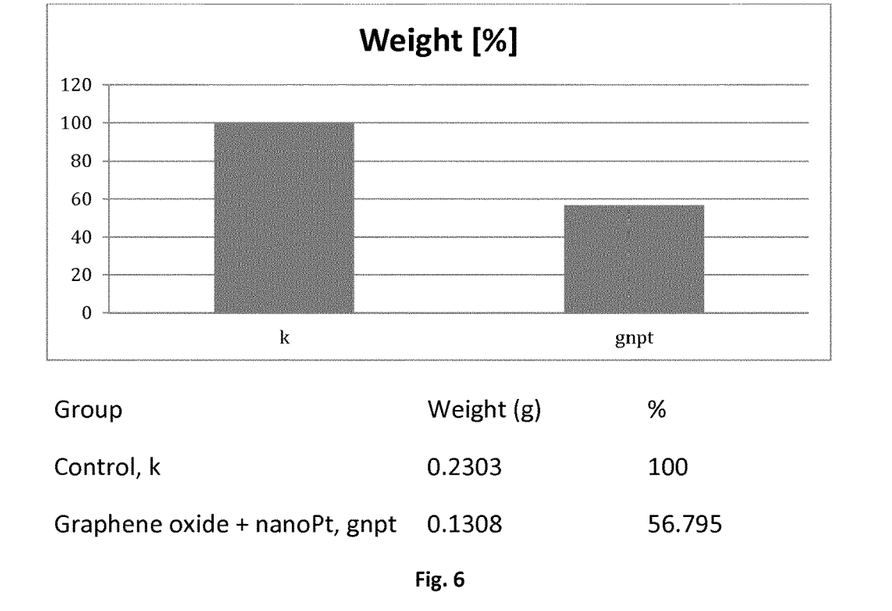
Figure 7:
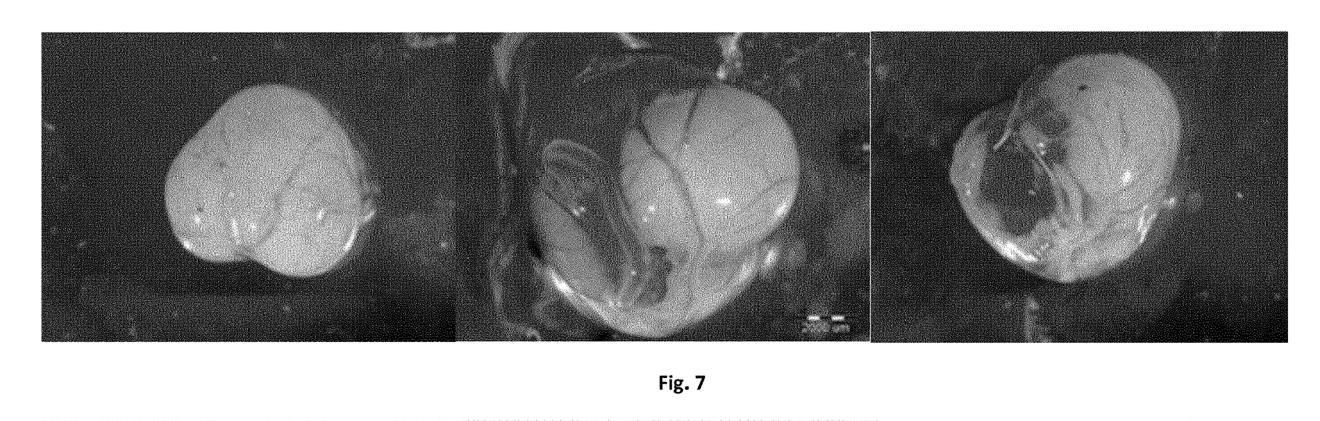
Figure 8:
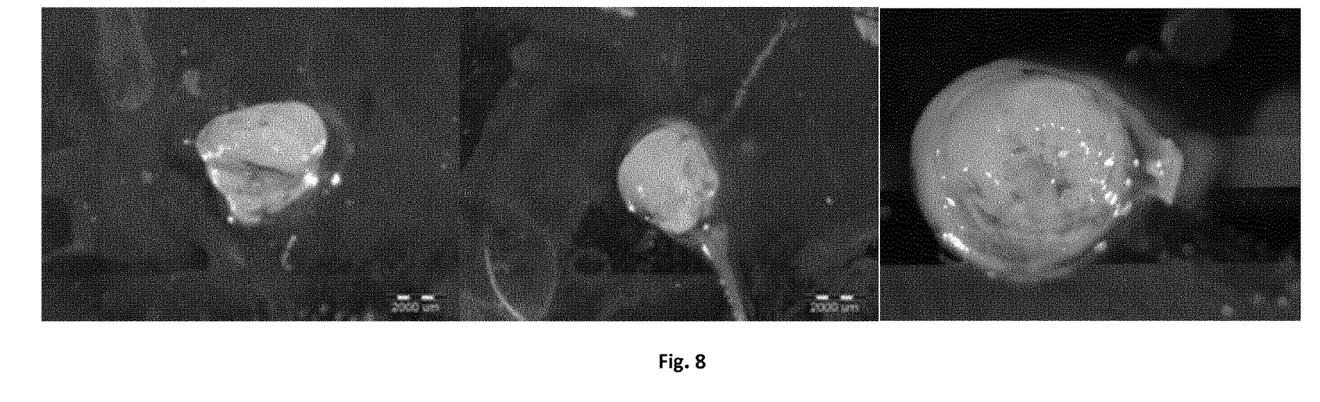

10 experiments were conducted, in which studied suspensions were administered to GM tumour derived from the cells of U-87 line, implanted and grown on the chorioallantoic membrane of the chicken embryo. It was found that:

1. graphene oxide flakes as well as Pt° nanoparticles in the study on U-87 glioblastoma multiforme tumours—as a result of direct injection into the tumour—allowed observation of reduction in weight and volume and activation of apoptosis signalling pathways;
2. graphene oxide flakes decorated with platinum nanoparticles (at all of the studied concentrations of graphene and platinum) administered to glioblastoma multiforme tumour activate programmed cell death through activation of caspase 9 (FIG. 3);
3. graphene oxide flakes decorated with Pt nanoparticles (at all of the studied concentrations of graphene and platinum) did not affect the induction of inflammation in GM tumour (FIG. 5);
4. graphene oxide flakes decorated with Pt nanoparticles (at all of the studied concentrations of graphene and platinum) affected the reduction of the weight of GM tumour on the level of 8.64% to 82% of the weight of control tumour (FIGS. 6, 7 and 8);
5. Our own (in vitro and in vivo) study showed that, in comparison to the control group, positive control group (cisplatin) and group with platinum nanoparticles and with graphene oxide flakes, graphene oxide nanoflakes with platinum nanoparticles attached exhibit higher toxicity in relation to cells and tumours of U-87 glioblastoma multiforme. At the same time, they exhibit lower toxicity for adjacent tissues due to its activity which is limited and concentrated in the tumour area.

The solution according to the present invention has the following advantages:

Platinum is present in the form of Pt(0) metal nanoparticles, which reduces its solubility and distribution in the organism, and is deposited on graphene oxide flakes, which allows for its safe transport and deposition within the tumour and successive releasing and binding to cellular DNA, which activates tumour cell apoptosis and tumour regression.

Pt nanoparticles, as opposed to platinum salts, have metal properties, do not dissolve in water, do not form salts. This limits the distribution of platinum via biological fluids and significantly reduces the toxicity of platinum for healthy tissues.

Platinum nanoparticles are transported across cell and nuclear membranes within 1-24 h.

As metal nanoparticles, they are distributed in the organism through a route alternative to the blood (from cell to cell through cell membrane), which may considerably limit the toxicity of platinum to the place of introduction of nanoparticles and its small surrounding areas.

Platinum nanoparticles react with DNA, which results in its degradation and activation of the process of cell death by apoptosis.

Graphene oxide allows targeted administration of platinum nanoparticles, limited to the location of graphene oxide.

Graphene oxide exhibits an affinity to the cell membrane of tumour cells, when introduced into the tumour, it tends to position itself at its central point, with minimal tendency to migration within the body.

Graphene oxide performs functions of not only the carrier of Pt nanoparticles but it also exhibits activation properties in tumour cells of the death process (apoptosis).

Combination of platinum nanoparticles with graphene oxide flakes conditions local activity of Pt(0) in place of its introduction.

Graphene oxide, being a material having very active surface and, in particular, edges, combines with platinum nanoparticles and it acts for them as a kind of raft and allows direct delivery of platinum nanoparticles to tumour cells by adhesion to their cell membranes.

Innovation in the use of platinum nanoparticles bound to graphene oxide flakes in therapy directed against tumours is manifested by controlling the area of activity, i.e. limitation of activation site of the mechanism of programmed cell death to the area of the tumour and, to a negligible extent, healthy cells (i.e. not undergone neoplastic transformation), adjacent to the tumour tissue. Control of the activity site allows limitation of toxic effects to the site of administration and elimination of toxic side effects resulting from the penetration of platinum nanoparticles into adjacent tissues and the bloodstream. Further, the nanoparticles, as a fragmented metal, exclude the possibility of creating toxic compounds in the bloodstream and of interacting with other medicines used collaterally in chemotherapy.

REFERENCES

[1] W. S. Hummers and R. E. Offeman, "Preparation of Graphitic Oxide", J. Am. Chem. Soc., vol. 80 (1958) 1339.
[2] D. C. Marcano, D. V. Kosynkin, J. M. Berlin, A. Sinitskii, Z. Sun, A. Slesarev, L. B. Alemany, W. Lu and J. M. Tour, "Improved synthesis of graphene oxide", ACS Nano, vol. 4 (2010) 4806-4814.
[3] O. C. Compton and S. T. Nguyen, "Graphene Oxide, Highly Reduced Graphene Oxide, and Graphene: Versatile Building Blocks for Carbon-Based Materials", Small, vol. 6 (2010) 711-723.
[4] A. Fakhri, "Adsorption characteristics of graphene oxide as a solid adsorbent for aniline removal from aqueous solutions: Kinetics, thermodynamics and mechanism studies", Journal of Saudi chemical Society, in press.
[5] S. H. Hsieh, M. C. Hsu, W. L. Liu, W. J. Chen, "Study of catalyst on graphene and its application to fuel cell", Applied Surface Science, vol. 277 (2013) 223-230.
[6] B. F. Machado, P. Serp, "Graphene-based materials for catalysis", Catalysis Science and Technology, vol. 2 (2012) 54-75.
[7] B. Seger, P. V. Kamat, "Electrocatalically active graphene-platinum nanocomposites. Role of 2-D carbon support in PEM fuel cells, The Journal of Chemical Chemistry C, vol. 113 (2009) 7990-7995.
[8] Y. Wang, J. Liu, D. D. Sun, "high-quality reduced graphene oxide-nanocrystalline platinum hybrid materials prepared by simultaneous co-reduction of grapheme oxide and chloroplatinic acid, Nanoscale Research Letters, vol. 6:241 (2011).
[9] Ch. Wang et al., "A unique platinum-graphene hybrid structure for high activity and durability in oxygen reduction reaction", Scientific Reports, vol. 3:2580 (2013).
[10] H. W. Chang et al., "Preparation of graphene-supported platinum nanoparticles in aqueous solutions by femtosecond laser pulses for methanol oxidation", Journal of Power Sources, vol. 239 (2013) 164-168.
[11] G. Yue et al., "Platinum/graphene hybrid film as a counter electrode for dye-sensitized solar cells", Electrochimica Acta, vol. 92 (2013) 64-70.
[12] Ch. Chen, L. MingCe, W. HaoDong, C. WeiMin, "One-step synthesis of Pt nanoparticles/reduced graphene oxide composite with enhanced electrochemical catalytic activity, Science China-Chemistry, vol. 56 (2013) 354-361.

[13] L. AiRong, H. ShiMing, "A glucose biosensor based on direct electrochemistry of glucose oxidase immobilized onto platinum nanoparticles modified graphene electrode, Science China-Physics, Mechanics and Astronomy, vol. 55 (2012) 1163-1167.

[14] F. Zhang et al., "Microwave-assisted synthesis of Pt/graphene nanocomposites for non enzymatic hydrogen peroxide sensor" Int. J. Electrochem. Sci., vol. 7 (2012) 1968-1977.

[15] Brandes A A, Basso U, Reni M, Vastola F, Tosoni A, Cavallo G, Scopece L, Ferreri A J, Panucci M G, Monfardini S, Ermani M. First-line chemotherapy with cisplatin plus fractionated temozolomide in recurrent glioblastoma multiforme: a phase II study of the Gruppo Italiano Cooperativo di Neuro-Oncologia. J Clin Oncol. 2004, 1; 22(9):1598-604.

[16] Boulikas T., Vougiouka M., Recent clinical trials Rusing cisplatin, carboplatin and their combination chemotherapy drugs. Oncol Rep 2004, 11: 559-595.

[17] Bencokova Z, Pauron L, Devic C, Joubert A, Gastaldo J, Massart C, Balosso J, Foray N. Molecular and cellular response of the most extensively used rodent glioma models to radiation and/or cisplatin. J Neurooncol. 2008, 86(1):13-21.

[18] Rachlin K, Moore D H, Yount G. Infrasound sensitizes human glioblastoma cells to cisplatin-induced apoptosis. Integr Cancer Ther. 2013, 12(6):517-27.

[19] Jung Y, Lippard S J. Direct cellular responses to platinum-induced DNA damage. Chem Rev. 2007, 107 (5):1387-407.

[20] Giavini, E., Lemonica, I. P., Lou, Y., Broccia, M. L. and Prati, M. Induction of micronuclei and toxic effects in embryos of pregnant rats treated before implantation with anticancer drugs: Cyclophosphamide, Cis-platinum, adriamycin. Teratog. Carcinog. Mutagen., 1990, 10: 417-426.

[21] Ognio E., Lapide M., Ottone M., Mandys V., Peterka M., Parodi B., Viale M. Embryo-lethal and teratogenic effect of the new platinum compound DPR in pregnant mice. Arch. of Tox., 2003, 77: 584-90.

[22] Podratz J L, Knight A M, Ta L E, Staff N P, Gass J M, Genelin K, Schlattau A, Lathroum L, Windebank A J. Cisplatin induced mitochondrial DNA damage in dorsal root ganglion neurons. Neurobiol Dis. 2011, 41: 661-8.

[23] Prasek, M., Sawosz, E., Jaworski, S., Grodzik, M., Ostaszewska, T., Komaszewski, M., Wierzbicki, M., Chwalibog, A. (2013) Influence of nanoparticles of platinum on chicken embryo development and brain morphology. *Nanoscale Research Letters*, 8, 251-260

[24] Sawosz E., Jaworski S., Kutwin M., Hotowy A., Wierzbicki M., Grodzik M., Kurantowicz N., Strojny B., Lipinska L., Chwalibog A. 2014 Toxicity of pristine graphene in experiments in a chicken embryo model. *International Journal of Nanomedicine*, 9, 3913-3922.

[25] Jaworski, S., Sawosz, E., Grodzik, M., Winnicka, A., Prasek, M., Wierzbicki, M., Chwalibog, A. 2013. In vitro evaluation of the effects of graphene platelets on globlastoma multiforme cells. *International Journal of Nanomedicine*, 8, 413-420.

[26] Hinzmann M., Jaworski S., Kutwin M., Jagiello J., Kozinski R., Wierzbicki M., Grodzik M., Lipinska L., Sawosz E., Chwalibog A. 2014. Nanoparticles containing allotropes of carbon have genotoxic effects on glioblastoma multiforme cells. *International Journal of Nanomedicine*, 9, 2409-2417.

The invention claimed is:

1. A method of treating human or animal tumors, the method comprising: depositing nanoparticles of aqueous colloidal metallic platinum in zero oxidation state on a surface of graphene oxide nanoflakes and forming a water suspension by using ultrasonic energy in an ultrasound bath thereof, wherein graphene oxide nanoflakes are present in the water suspension in a range of about 100 µg/ml to about 500 µg/ml and nanoparticles of metallic platinum are present in the suspension in a range of about 5 µg/ml to about 50 µg/ml, wherein platinum nanoparticles and graphene oxide nanoflakes are bound together through electronic interactions and graphene oxide nanoflakes and platinum nanoparticles are non-reduced in the water suspension, administering the water suspension of non-reduced graphene oxide nanoflakes and nanoparticles of metallic platinum to human or animal tumors by direct injection of the water suspension into the tumor or area directly surrounding the tumor, wherein the water suspension functions as an antitumor agent.

* * * * *